(12) United States Patent
Edgell et al.

(10) Patent No.: US 8,784,143 B2
(45) Date of Patent: Jul. 22, 2014

(54) CANTILEVERED SPRING CONTACT FOR AN IMPLANTABLE MEDICAL DEVICE

(75) Inventors: John M. Edgell, Plymouth, MN (US); David M. Flynn, Lino Lakes, MN (US); John E. Hansen, Ham Lake, MN (US); Michael J. Kloosterboer, Minneapolis, MN (US); Lawrence D. Swanson, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 106 days.

(21) Appl. No.: 13/435,271

(22) Filed: Mar. 30, 2012

(65) Prior Publication Data

US 2012/0271387 A1 Oct. 25, 2012

Related U.S. Application Data

(60) Provisional application No. 61/477,302, filed on Apr. 20, 2011.

(51) Int. Cl.
*H01R 13/187* (2006.01)

(52) U.S. Cl.
USPC .......................................... 439/843; 439/246

(58) Field of Classification Search
USPC ................................ 439/843, 246
See application file for complete search history.

(56) References Cited

U.S. PATENT DOCUMENTS

| | | |
|---|---|---|
| 2,659,876 A | 11/1953 | Dupre et al. |
| 3,238,496 A | 3/1966 | Crowther |
| 3,304,392 A | 2/1967 | Isler |
| 3,891,298 A | 6/1975 | Yorgin et al. |
| 3,908,668 A | 9/1975 | Bolduc |
| 4,583,543 A | 4/1986 | Peers-Trevarton |
| 4,764,132 A | 8/1988 | Stutz, Jr. |
| 4,806,113 A | 2/1989 | Rate, Jr. et al. |
| 5,005,104 A | 4/1991 | Grunert et al. |
| 5,076,270 A | 12/1991 | Stutz, Jr. |
| 5,667,413 A * | 9/1997 | Trafton .......................... 439/843 |
| 5,669,790 A | 9/1997 | Carson et al. |
| 5,681,187 A * | 10/1997 | Fukushima et al. .......... 439/700 |
| 5,730,628 A * | 3/1998 | Hawkins ........................ 439/843 |
| 5,989,077 A | 11/1999 | Mast et al. |
| 6,250,974 B1 * | 6/2001 | Kerek ............................ 439/843 |

(Continued)

FOREIGN PATENT DOCUMENTS

| | | |
|---|---|---|
| EP | 0261582 A1 | 3/1988 |
| EP | 0357941 A2 | 3/1990 |
| WO | WO-9916503 A1 | 4/1999 |

*Primary Examiner* — Gary Paumen
(74) *Attorney, Agent, or Firm* — Schwegman Lundberg & Woessner, P.A.

(57) ABSTRACT

Some examples of an electrical contact spring for an implantable medical device includes a housing, rigid and tubular in shape, defining a housing passage extending along a longitudinal axis, from a proximal portion including a proximal lip that defines a proximal opening, to a distal portion including a distal lip that defines a distal opening and a spring disposed in the housing, the spring tubular in shape and defining a spring passage concentric to the housing passage, the spring including: a distal ring portion disposed adjacent the distal portion of the housing and physically coupled to the housing, a plurality of spring elements coupled to and extending from the distal ring portion toward the proximal portion of the housing and a proximal ring portion disposed adjacent the proximal portion of the housing, cantilevered and suspended inside of and spaced apart from the housing by the plurality of spring elements.

16 Claims, 14 Drawing Sheets

(56) References Cited

U.S. PATENT DOCUMENTS

| | | |
|---|---|---|
| 6,254,439 B1 * | 7/2001 | Endo et al. .................... 439/843 |
| 6,482,049 B1 * | 11/2002 | Swearingen ................. 439/843 |
| 7,003,351 B2 | 2/2006 | Tvaska et al. |
| 7,035,689 B1 | 4/2006 | Hawkins et al. |
| 7,047,077 B2 | 5/2006 | Hansen et al. |
| 7,387,548 B2 * | 6/2008 | Takehara et al. ............. 439/843 |
| 7,462,078 B2 * | 12/2008 | Mao ............................. 439/843 |
| 8,142,238 B2 * | 3/2012 | Heigl et al. ................... 439/843 |
| 2004/0033732 A1 * | 2/2004 | Koch, Jr. ....................... 439/843 |
| 2006/0264122 A1 | 11/2006 | Aman et al. |
| 2007/0099518 A1 | 5/2007 | Arnholt et al. |
| 2009/0012576 A1 * | 1/2009 | Erbstoeszer et al. ........... 607/38 |
| 2010/0285697 A1 | 11/2010 | Zart et al. |
| 2010/0324844 A1 | 12/2010 | Marti |

* cited by examiner

CANTILEVERED SPRING CONTACT FOR AN IMPLANTABLE MEDICAL DEVICE

CROSS-REFERENCE TO RELATED APPLICATION

This application claims the benefit of U.S. Provisional Application No. 61/477,302, filed on Apr. 20, 2011, under 35 U.S.C. §119(e), which is hereby incorporated by reference in its entirety.

TECHNICAL FIELD

This document relates generally to electrical connectors for implantable medical devices and particularly to a cantilevered electrical contact spring for an implantable medical device.

BACKGROUND

Electrical leads are coupled to and decoupled from a terminal of an implantable medical device by hand pressure applied to the proximal portion of an electrical lead. Because these electrical leads are often coupled and decoupled in use, sometimes in misalignment, it is important to provide components that do not undesirably fatigue or fail because of coupling or decoupling.

SUMMARY

Some examples include a housing that is rigid, defining a housing passage extending along a longitudinal axis, from a proximal portion including a proximal lip that defines a proximal opening, to a distal portion including a distal lip that defines a distal opening and an electrical contact spring disposed in the housing. In some examples, the electrical contact spring defines an electrical contact spring passage concentric to the housing passage. In some examples, the electrical contact spring includes a distal ring portion disposed adjacent the distal portion of the housing and physically coupled to the housing. In some examples, the electrical contact spring includes a proximal ring portion disposed near the proximal portion of the housing, cantilevered and suspended inside of and spaced apart from the housing by a plurality of electrical contact spring elements coupled to and extending from the distal ring portion to the proximal ring portion.

Some examples include a method for connecting an implantable electrical lead to an implantable medical device, the method including forming a housing in the implantable medical device, comprising forming a housing passage, the housing passage extending along a longitudinal axis, from a proximal portion defining a proximal opening, to a distal portion defining a distal opening. Some examples include forming an electrical contact spring by coupling a distal ring portion to a proximal ring portion with a plurality of electrical contact spring elements extending from the distal ring portion to the proximal portion. Some examples include disposing the electrical contact spring in the housing, with the proximal ring portion coupled to the housing adjacent the proximal portion of the housing. Some examples include suspending the proximal ring portion inside of and spaced apart from the housing, the proximal ring portion cantilevered by the plurality of electrical contact spring elements. Some examples include inserting the implantable electrical lead into the electrical contact spring, flexing at least some of the plurality of electrical contact spring elements and moving the proximal ring portion with respect to the housing.

Some examples include a hermetically sealed implantable medical device, a header coupled to the hermetically sealed medical device, a housing, coupled to the header, inside the header, the housing tubular in shape, defining a housing passage extending along a longitudinal axis, from a proximal portion including a proximal lip that defines a proximal opening, to a distal portion including a distal lip that defines a distal opening and an electrical contact spring disposed in the housing, the electrical contact spring tubular in shape and defining an electrical contact spring passage concentric to the housing passage. In some examples, the electrical contact spring includes a distal ring portion disposed adjacent the distal portion of the housing and physically coupled to the housing. In some examples, the electrical contact spring includes a proximal ring portion disposed near the proximal portion of the housing, suspended inside of and spaced apart from at least some of the housing by a plurality of electrical contact spring elements coupled to and extending from the distal ring portion to the proximal ring portion, wherein the plurality of electrical contact spring elements are adapted to flex to move transversely with respect to the longitudinal axis, to move the proximal ring portion with respect to the housing. In some examples, the electrical contact spring includes an electrical lead disposed in the electrical contact spring passage, with at least some of the plurality of electrical contact spring elements deformed around the electrical lead, contacting an electrical contact of the electrical lead.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

The following detailed description of the present invention refers to subject matter in the accompanying drawings that shows, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Operation of an implantable medical device such as a pacemaker or defibrillator involves the transmission of electrical energy, generated by the device, to body tissue such as the heart. In some instances, this energy is conducted over an electrical lead. An electrical lead, according to some examples, includes fatigue-resistant, insulated electrical conductor designed to endure implantation in the human body environment. In some examples, the distal portion of the electrical lead includes an electrode. The distal portion fixes to heart tissue, such as with anchoring tines, in some examples. According to some examples, the proximal portion of the electrical lead is connected to a terminal of the device.

The present subject matter provides examples of an improved electrical contact spring to mechanically and electrically contact an electrical terminal of an electrical lead when the electrical lead is coupled as part of the device. The electrical contact spring is adapted to allow for the electrical lead to be coupled to the device, and decoupled from the device, establishing electrical contact with the electrical lead during coupling, and elastically returning to form after decoupling. The present subject matter is improved as it decreases instances in which the electrical contact spring is flexed beyond its elastic limit, for example.

Figure 1:
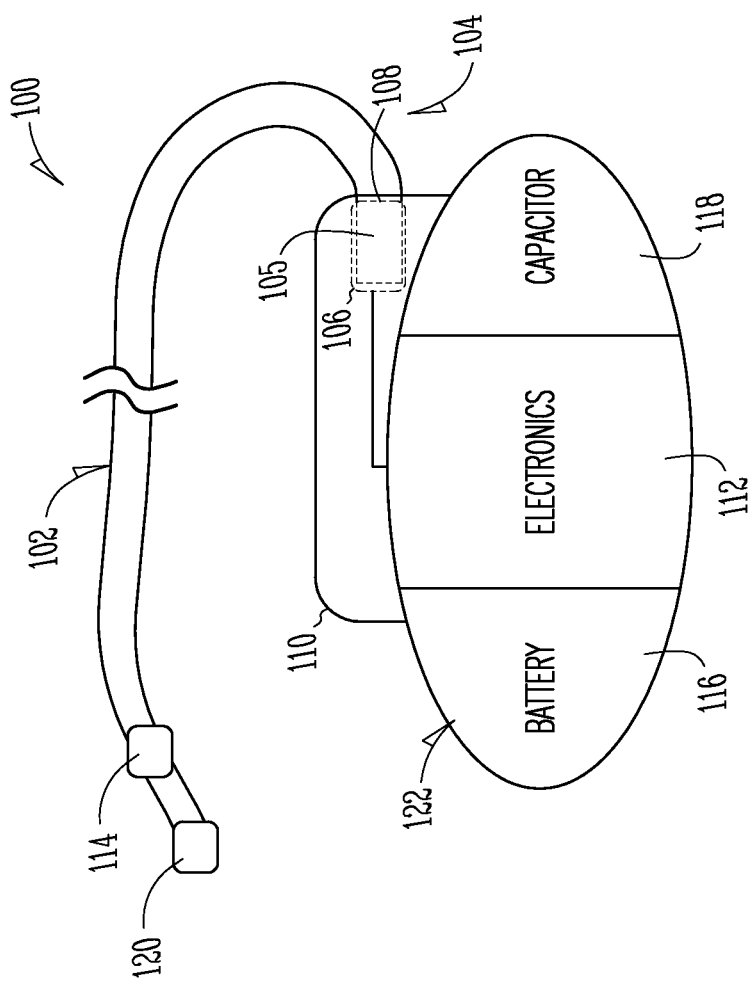
FIG. 1 is a schematic of a medical system including a cantilevered spring contact, according to some examples.

FIG. 1 is a schematic of a medical system including a cantilevered spring contact, according to some examples. The medical system 100 is adapted to provide therapeutic stimulus, such as to a heart. Examples of medical systems contemplated herein include, but are not limited to, implantable pacemakers, implantable defibrillators, implantable nerve stimulation devices and devices that provide stimulation from outside the body, including, but not limited to, external defibrillators.

In various examples, an electrical lead 102 includes a proximal portion 104. In some examples, the proximal portion 104 includes a male terminal such as a pin-shaped electrical terminal 105. Materials used to construct the electrical lead 102 are biocompatible, in several examples. According to various examples, portions of the electrical lead include a conductor that is electrically insulated, such as with silicone rubber, epoxy, or polyurethane. Conductors for electrical leads include, but are not limited to, titanium and its alloys, 316L stainless steel and its alloys, or platinum and its alloys.

Electrical contact between the electrical lead and the device is through a female electrical contact spring 106 disposed in a connector electrical lead opening 108 of a device header 110, according to certain examples. Although the illustration provides a male terminal on the electrical lead, and a female terminal on the device, the present subject matter is not so limited, and extends to configurations in which the male terminal is part of the device, and the electrical lead includes the female terminal.

Electrical contact springs, in various examples, are adapted to maintain a minimum contact force with the electrical lead to provide an electrical path having improved reliability of conduction. A contact force, such as a minimum contact force, is maintained through elastic deformation of the electrical contact spring. In some instances, such as after several insertions and extractions of the electrical lead from the device, or in instances when a misaligned or over-sized electrical lead is inserted into the electrical lead opening, an electrical contact spring deforms inelastically. Such deformation can affect the reliability of the electrical contact to the electrical lead. For example, the electrical contact spring can permanently deform to a shape that is out of contact with an electrical contact portion of the electrical lead. In some examples, permanent deformation occurs when an electrical contact spring is over pushed beyond its elastic limit, i.e. its yield.

By way of several examples, the present subject matter provides an electrical contact spring 106 adapted to elastically flex to many shapes. Examples disclosed herein provide an electrical contact spring 106 that accommodates electrical lead misalignment during electrical lead coupling. In some examples, the present subject matter provides an electrical contact spring that has low insertion and extraction forces. In some examples, the present subject matter provides an electrical contact spring that has a plurality of contact points. A plurality of contact point provides redundancy of connections and improves electrical conductivity between electrical contact spring (and by association the implantable medical device) and the electrical lead.

The medical system 100, in several examples, includes a number of additional components. Various examples include electronics 112. In various examples, the electronics 112 are adapted to monitor a patient, such as by monitoring a sensor 114, and to monitor and control activity within the medical system 100. In some examples, the electronics 112 are to monitor a patient, diagnose a condition to be treated such as an arrhythmia, and control delivery of a stimulation pulse of energy to the patient. In various examples, the electrical lead 102 is to contact patient tissue with a stimulation electrode 120, which provides electrical contact to the patient. Examples of the electrical lead 102 use different numbers of stimulation electrodes and/or sensors in accordance with the parameters of the therapy to be performed. The electronics 112 can be powered wirelessly using an inductor. Alternatively, or in addition to, the electronics 112 can be powered by a battery 116.

In some examples, electronics 112 are to direct therapeutic bursts of energy to a patient from the battery 116. For therapies, such as defibrillation, that discharge energy amounts exceeding what battery 116 is able to provide alone at a specified rate, a capacitor 118 is used to provide or augment an energy pulse. In some examples, energy from the battery 116 is controlled by the electronics 112 to charge the capacitor 118. The capacitor 118 is controlled by the electronics 112 to discharge to a patient to treat the patient. In certain examples, the electronics 112 include an electronic cardiac rhythm management circuit coupled to the battery 116 and the capacitor 118 to discharge the capacitor 118 to provide a therapeutic defibrillation pulse.

A hermetically sealed device can 122 houses components, such as the battery 116, the electronics 112, and the capacitor 118, in some examples. Hermeticity is provided by welding components into the hermetically sealed device can 122, in some examples. Other examples bond portions of the can 122 together with an adhesive such as a resin based adhesive such as epoxy. Some examples of the can 122 include an epoxy sealed seam or port. Several materials can be used to form the can 122, including, but not limited to, titanium, stainless steel, nickel, a polymeric material, or combinations of these materials. In various examples, the can 122 is biocompatible.

Figure 2:
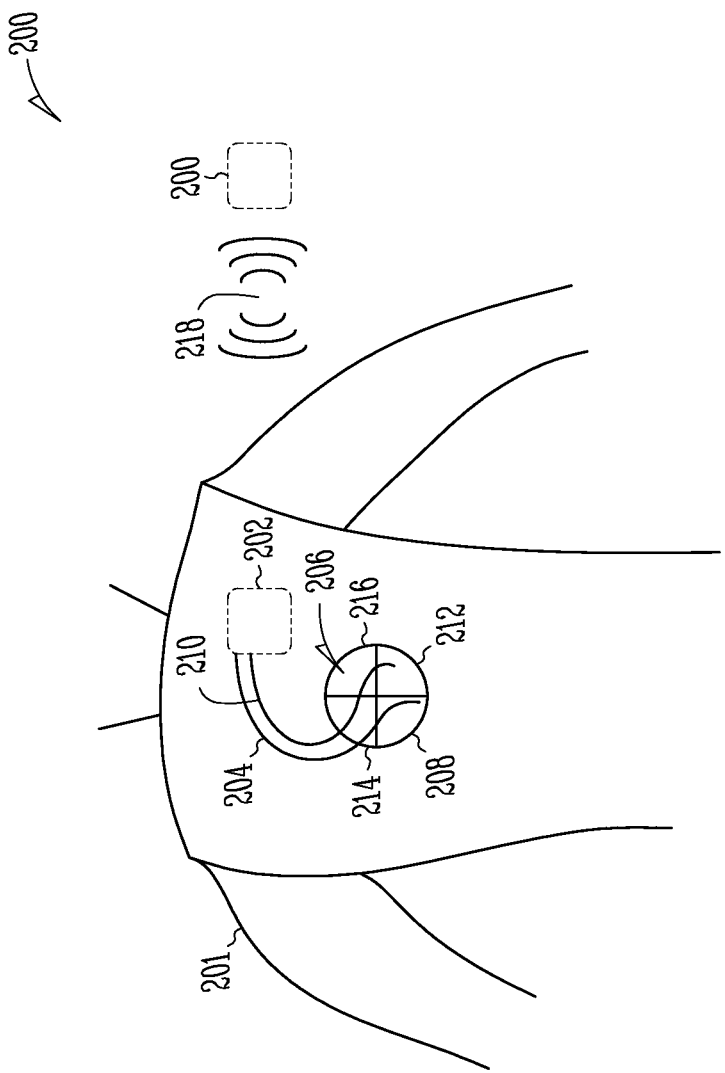
FIG. 2 shows a diagram of an implanted medical system including a cantilevered spring contact, according to some examples.

FIG. 2 shows a diagram of an implanted medical system 200 including a cantilevered spring contact, according to some examples. The system 200 includes a cardiac rhythm management device 202 coupled to a first electrical lead 204 to extend through the heart 206 to the right ventricle 208 to stimulate at least the right ventricle 208. The system also includes a second electrical lead 210 to extend through the heart 206 to the left ventricle 212. In various examples, one or both of the first electrical lead 204 and the second electrical lead 210 include electrodes to sense intrinsic heart signals and to stimulate the heart. The first electrical lead 204 is in direct contact (e.g., touching) with the right atrium 214 and the right ventricle 208 to sense and/or stimulate both those tissue regions. The second electrical lead 210 is in direct contact with the left atrium 216 and the left ventricle 212 to sense and/or stimulate both those tissue regions. The cardiac rhythm management device 202 uses the electrical lead electrodes to deliver energy to the heart, either between electrodes on the electrical leads or between one or more electrical lead electrodes and the cardiac rhythm management device 202. In some examples, the cardiac rhythm management device 202 is programmable and wirelessly communicates 218 programming information with a programmer 220. In some examples, the programmer 220 wirelessly 218 charges an energy storage device of the cardiac rhythm management device 202.

Figure 3:
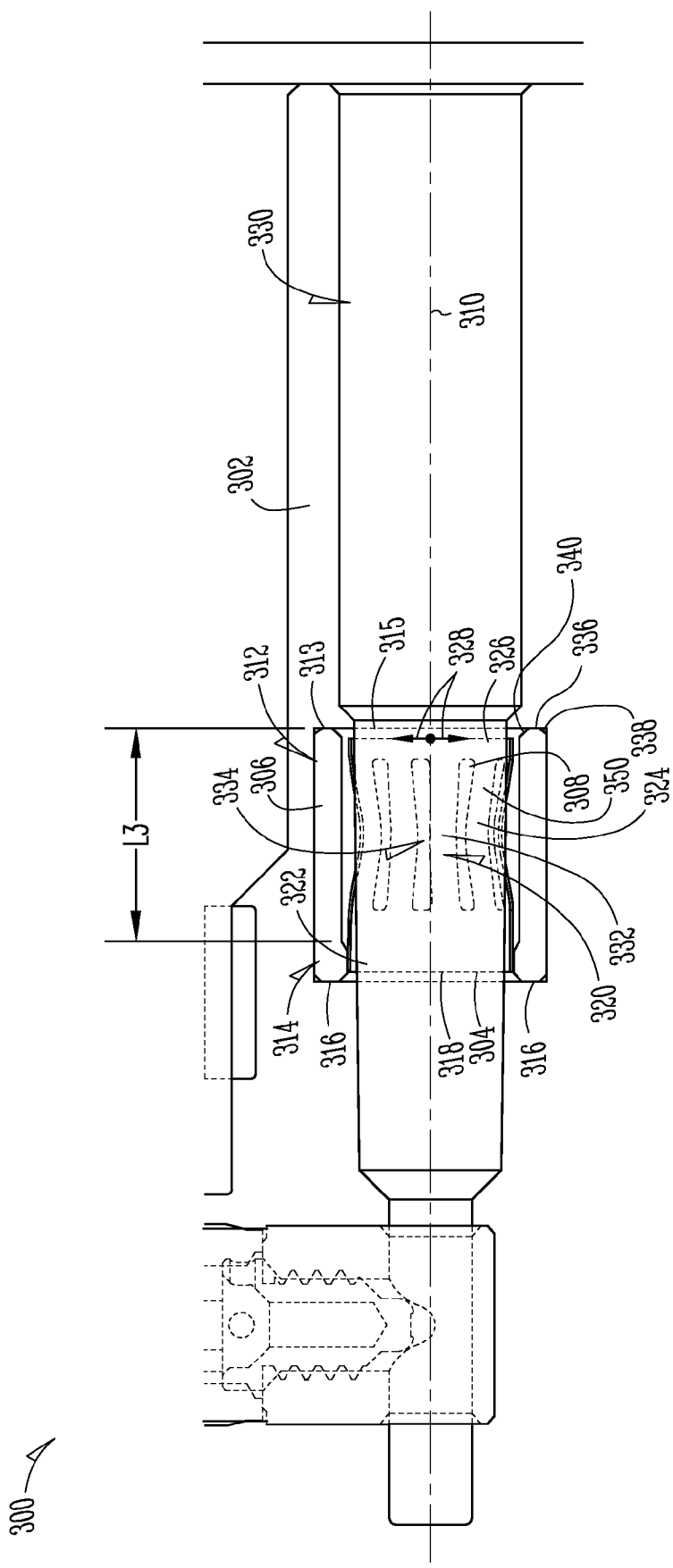
FIG. 3 shows a longitudinal cross section of a device header, an electrical lead, and a spring, according to some examples.

FIG. 3 shows a longitudinal cross section of a device header, an electrical lead, and a spring, according to some examples. According to several examples, the header 302 is coupled to a hermetically sealed medical device, such as to a metallic can, such as through solder, epoxy and the like. Various examples include an assembly that couples an electrical contact spring 304 to the header 302. Certain examples include a housing 306, coupled to the header 302, such as inside the header 302. In various examples, the housing 306 is tubular in shape and defines a housing passage 308 extending along a longitudinal axis 310, from a proximal portion 312 including a proximal lip 313 that defines a proximal opening 315, to a distal portion 314 including a distal lip 316 that defines a distal opening 318.

The electrical contact spring 304 coupled to the housing 306. In various examples, the electrical contact spring 304 is disposed at least partially inside the housing 306. The electrical contact spring 304 is tubular in shape in some examples. In certain examples, the electrical contact spring 304 defines an electrical contact spring passage 320. In some examples, the electrical contact spring passage 320 is concentric to the housing passage 308. In some examples, the housing 306 is formed of a polymer insert molded over a metallic portion, with the proximal lip 313 and the distal lip 316 formed of the polymer.

In various examples, the electrical contact spring 304 includes a distal ring portion 322. In various examples, the distal ring portion 322 is disposed adjacent the distal portion 314 of the housing 306. In some examples, the distal ring portion 322 abuts the housing 306. In some examples, the distal ring portion 322 is physically coupled to the housing 306. Examples of such a physical coupling include, but are not limited to, an adhesive, a press fit, a threaded engagement, a weld, including a spot weld, and instances in which the electrical contact spring 304 is formed integrally with the housing 306, that is, they are formed from the same starting material, such as bar stock or the like. In various examples, the electrical contact spring 304 is formed of a metallic alloy. In some examples, the spring is formed of MP35N.

Various examples include a proximal ring portion 326 disposed near the proximal portion 312 of the housing 306, suspended inside of and spaced apart from at least some of the housing 306 by an electrical spring contact 304 that includes a plurality of electrical contact spring elements 324 coupled to and extending from the distal ring portion toward the proximal portion of the housing. In some examples, the plurality of spring elements is circumferentially spaced around the longitudinal axis 310, substantially equidistant from one another. In various examples, the plurality of electrical contact spring elements 324 are adapted to flex to move transversely 328 with respect to the longitudinal axis, to move the proximal ring portion 326 with respect to the housing 306. In various examples, the proximal opening 315 is larger than a perimeter or circumference of the proximal ring portion 326, according to some examples.

The shape or contour of the proximal opening 315, defined at the proximal portion 312 by the proximal lip 313, is maintained or regular along a length L3 of the contact spring 304, according to some examples. In some examples, the length L3 is maintained or regular until it narrows near the distal portion 314 to meet with the contact spring 304 near the distal ring portion 322, according to some examples. In various examples, the distal lip 316 defines a distal opening 318 that is smaller in perimeter than other portions of the housing 306. The distal ring portion 322 is sized to meet the distal lip 316 in some example. In some examples, the distal ring portion 314 has the same diameter as the proximal ring portion 326. In additional examples, the distal ring portion 314 is larger or smaller than the proximal ring portion 326.

In some examples, the proximal lip 313 is curved, having a cross-section that is semi-circular in shape. In some examples, including the illustration, the proximal lip 313 defines a flat portion 336 flanged on the inside and outside of the proximal opening 315 by angled linear portions 338, 340.

In some examples, an electrical lead 330 is disposed in the electrical contact spring passage 320, with at least some of the plurality of electrical contact spring elements 324 deformed around the electrical lead 330, contacting an electrical contact 332 of the electrical lead 330. The plurality of electrical contact spring elements 324 are elastically deformed while the electrical lead 330 is disposed in the electrical contact spring passage 308, according to several examples.

In some examples, each respective center portion 334 of each electrical contact spring element 324 physically contacts the electrical lead 330 in electrical conduction when the electrical lead 330 is inserted into place in the electrical contact spring passage 308, substantially aligned with the longitudinal axis 310. In some examples, an electrical contact spring element 324 includes leaf electrical contact spring. In some examples, the proximal ring portion 326 is completely spaced apart from the housing 306. In various examples, a respective center portion extends toward the longitudinal axis 310, nearer the longitudinal axis than is the distal ring portion 322. In various examples, a respective center portion extends toward the longitudinal axis 310, nearer the longitudinal axis than is the proximal ring portion 326. In some examples, a center portions includes linear ramps or side portions 350. Some examples include a center contact portion, such as the electrical contact 332. In some examples, the center contact portion is parallel to the longitudinal axis 310. In some examples, the center contact portion is nearer to the longitudinal axis than is the proximal ring portion 326.

In some examples, the header 302 is molded around the housing 306. Examples of molding include, but are not limited to, insert molding, forming an epoxy mold, and other moldings. In some examples, the proximal lip 313 is sized to receive the electrical lead 330 without contacting the electrical lead 330.

Figure 4:
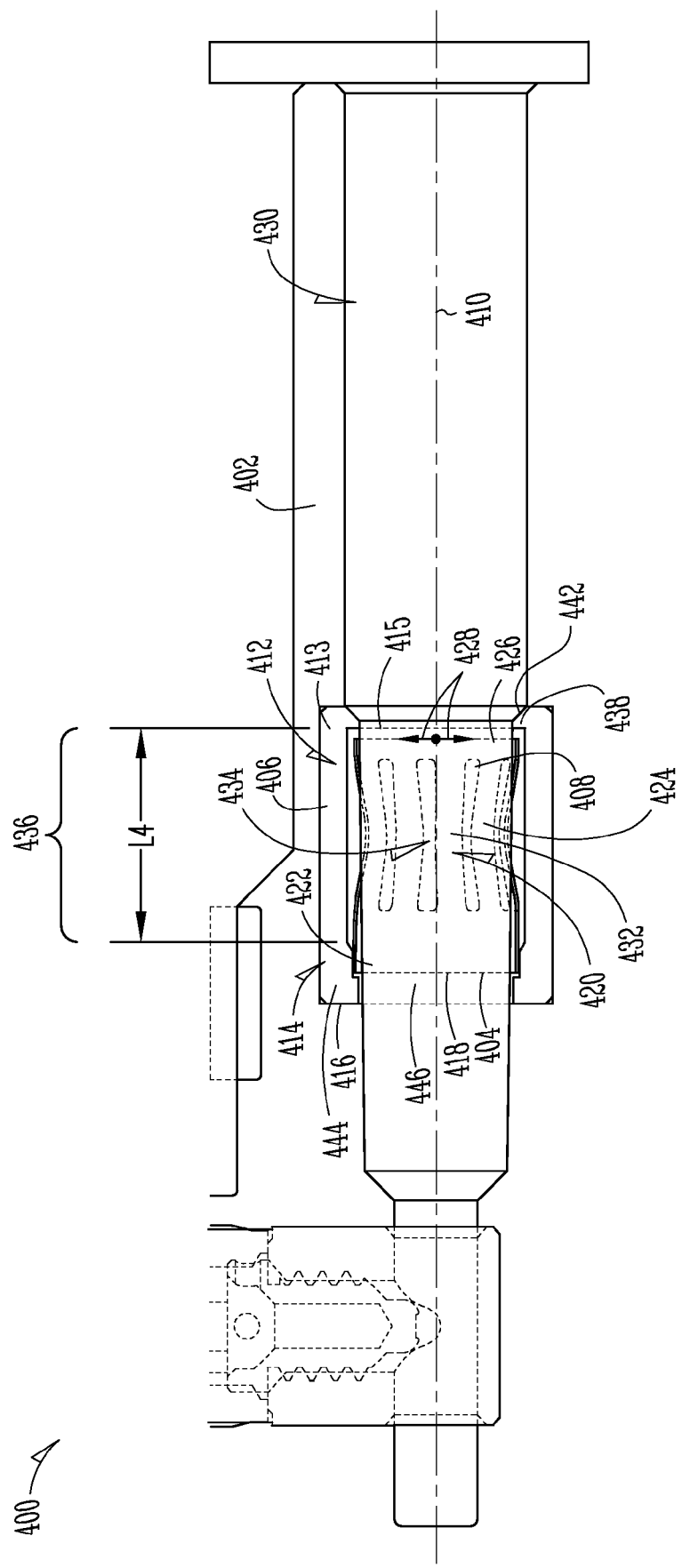
FIG. 4 shows a longitudinal cross section of an implantable medical device, an electrical lead, and a spring, and a housing that extends longitudinally beyond the spring according to some examples.

FIG. 4 shows a longitudinal cross section of an implantable medical device, an electrical lead, and a spring, and a housing that extends longitudinally beyond the spring according to some examples. Various examples include a housing 406, coupled to the header 402, such as inside the header 402. In various examples, the housing 406 is tubular in shape and defines a housing passage 408 extending along a longitudinal axis 410, from a proximal portion 412 including a proximal lip 413 that defines a proximal opening 415, to a distal portion 414 including a distal lip 416 that defines a distal opening 418.

The electrical contact spring 404 coupled to the housing 406. In various examples, the electrical contact spring is disposed at least partially inside the housing 406. The electrical contact spring 404 is tubular in shape in some examples. In certain examples, the electrical contact spring 404 defines an electrical contact spring passage 420. In some examples, the electrical contact spring passage 420 is concentric to the housing passage 408.

In various examples, the electrical contact spring 404 includes a distal ring portion 422. In various examples, the distal ring portion 422 is disposed adjacent the distal portion 414 of the housing 406. In some examples, the distal ring portion 422 abuts the housing 406. In some examples, the distal ring portion 422 is physically coupled to the housing 406. Examples of such a physical coupling include, but are not limited to, an adhesive, a press fit, a threaded engagement, a weld, including a spot weld, and instances in which the electrical contact spring 404 is formed integrally with the housing 406, that is, they are formed from the same starting material.

Various examples include a proximal ring portion 426 disposed near the proximal portion 412 of the housing 406, suspended inside of and spaced apart from at least some of the housing 406 by an electrical spring contact 404 that includes a plurality of electrical contact spring elements 424 coupled to and extending from the distal ring portion toward the proximal portion of the housing. In various examples, the plurality of electrical contact spring elements 424 are adapted to flex to move transversely 428 with respect to the longitudinal axis, to move the proximal ring portion 426 with respect to the housing 406.

In various examples, the shape or contour of the proximal opening 415, defined at the proximal portion 412 by the proximal lip 413, is smaller than an interior portion 436 of the contact housing 406. In various examples, a proximal protrusion 438 extends inward, toward the longitudinal axis 410. In various examples, an opening 446 defined by the proximal protrusion 438 is approximately the same diameter as the proximal ring portion. In some examples, the proximal protrusion 438 includes a ramp 442. The housing passage 408, including the contact spring 404 and the proximal lip 413 has a minimum diameter substantially equal to the diameter defined by the proximal protrusion 438. In some examples, this allows for a lead to enter the housing passage 408, misaligned with the longitudinal axis 410, and to avoid contacting the sharp edge of the proximal ring portion 426.

In some examples, the distal ring portion 422 is abuts a distal protrusion 444. In some examples, such an abutment resists longitudinal translation of the contact spring 404 distally with respect to the contact housing 408.

In some examples, an electrical lead 430 is disposed in the electrical contact spring passage 420, with at least some of the plurality of electrical contact spring elements 424 deformed around the electrical lead 430, contacting an electrical contact 432 of the electrical lead 430. The plurality of electrical contact spring elements 424 are elastically deformed while the electrical lead 430 is disposed in the electrical contact spring passage 420, according to several examples.

In some examples, each respective center portion 434 of each electrical contact spring element 424 physically contacts the electrical lead 430 in electrical conduction when the electrical lead 430 is inserted into place in the electrical contact spring passage 408, substantially aligned with the longitudinal axis 410. In some examples, the proximal ring portion 426 is completely spaced apart from the housing 406.

In some examples, the header 402 is molded around the housing 406. Examples of molding include, but are not limited to, insert molding, forming an epoxy mold, and other moldings. In some examples, the proximal lip 413 is sized to receive the electrical lead 430 without contacting the electrical lead 430.

Figure 5:
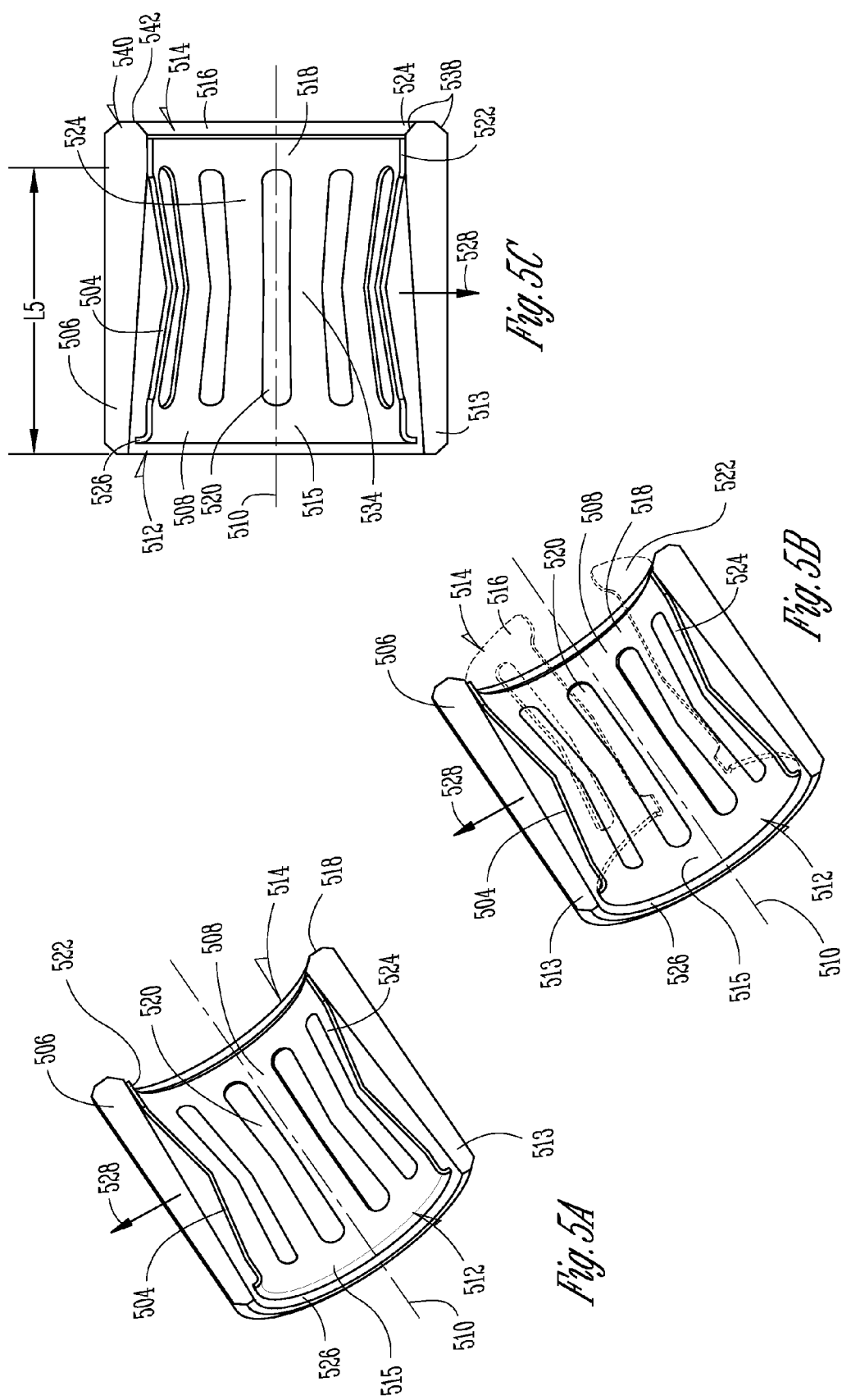
FIG. 5A shows a perspective view of a cross section of a spring and a housing, according to some examples.
FIG. 5B shows a perspective view of a cross section of a spring and a housing, showing wireframe of the spring, according to some examples.
FIG. 5C shows a longitudinal cross section of a spring and a housing, according to some examples.

FIGS. 5A-5B show views of a cross section of a spring and a housing, according to some examples. Various examples include a housing 506, couplable to a header, such as inside the header. In various examples, the housing 506 is tubular in shape and defines a housing passage 508 extending along a longitudinal axis 510, from a proximal portion 512 including a proximal lip 513 that defines a proximal opening 515, to a distal portion 514 including a distal lip 516 that defines a distal opening 518.

The electrical contact spring 504 coupled to the housing 506. In various examples, the electrical contact spring is disposed at least partially inside the housing 506. The electrical contact spring 504 is tubular in shape in some examples. In certain examples, the electrical contact spring 504 defines an electrical contact spring passage 520. In some examples, the electrical contact spring passage 520 is concentric to the housing passage 508.

In various examples, the electrical contact spring 504 includes a distal ring portion 522. In various examples, the distal ring portion 522 is disposed adjacent the distal portion 514 of the housing 506. In some examples, the distal ring portion 522 abuts the housing 506. In some examples, the distal ring portion 522 is physically coupled to the housing 506. Examples of such a physical coupling include, but are not limited to, an adhesive, a press fit, a threaded engagement, a weld, including a spot weld, and instances in which the electrical contact spring 504 is formed integrally with the housing 506, that is, they are formed from the same starting material.

Various examples include a proximal ring portion 526 disposed near the proximal portion 512 of the housing 506, suspended inside of and spaced apart from at least some of the housing 506 by an electrical spring contact 504 that includes a plurality of electrical contact spring elements 524 coupled to and extending from the distal ring portion 522 toward the proximal portion of the housing. In various examples, the plurality of electrical contact spring elements 524 are adapted to flex to move transversely 528 with respect to the longitudinal axis, to move the proximal ring portion 526 with respect to the housing 506. In various examples, the proximal opening 515 is larger than a perimeter or circumference of the proximal ring portion 526, according to some examples.

The shape or contour of the proximal opening 515, defined at the proximal portion 512 by the proximal lip 513, is tapered along a length L5 of the contact spring 504, according to some examples. In some examples, the length L5 is tapered to the distal portion 514 to meet with the contact spring 504 near the distal ring portion 522, according to some examples. In various examples, the distal lip 516 defines a distal opening 518 that is smaller in perimeter than other portions of the housing 506. The distal ring portion 522 is sized to meet the distal lip 516 in some example. In some examples, the distal ring portion 514 has the same diameter as the proximal ring portion 526. In additional examples, the distal ring portion 514 is larger or smaller than the proximal ring portion 526.

In various examples, the proximal ring portion 526 includes an annulus 540 that curves into the spring passage 520. For example, an annulus includes a face 542 that is transverse to the longitudinal axis 510, curving into a remainder of the proximal ring portion 526 that includes a face parallel to the longitudinal axis 510.

In some examples, the proximal lip 513 is curved, having a cross-section that is semi-circular in shape. In some examples, including the illustration, the proximal lip 513 defines a flat portion 536 flanged on the inside and outside of the proximal opening 515 by angled linear portions 538.

In some examples, an electrical lead is disposed in the electrical contact spring passage 520, with at least some of the plurality of electrical contact spring elements 524 deformed around the electrical lead, contacting an electrical contact of the electrical lead. The plurality of electrical contact spring elements 524 are elastically deformed while the electrical lead is disposed in the electrical contact spring passage, according to several examples.

In some examples, each respective center portion 534 of each electrical contact spring element 524 physically contacts the electrical lead in electrical conduction when the electrical lead is inserted into place in the electrical contact spring passage 520, substantially aligned with the longitudinal axis 510. In some examples, the proximal ring portion 526 is completely spaced apart from the housing 506.

In some examples, the header is molded around the housing 506. Examples of molding include, but are not limited to, insert molding, forming an epoxy mold, and other moldings.

Figure 6:
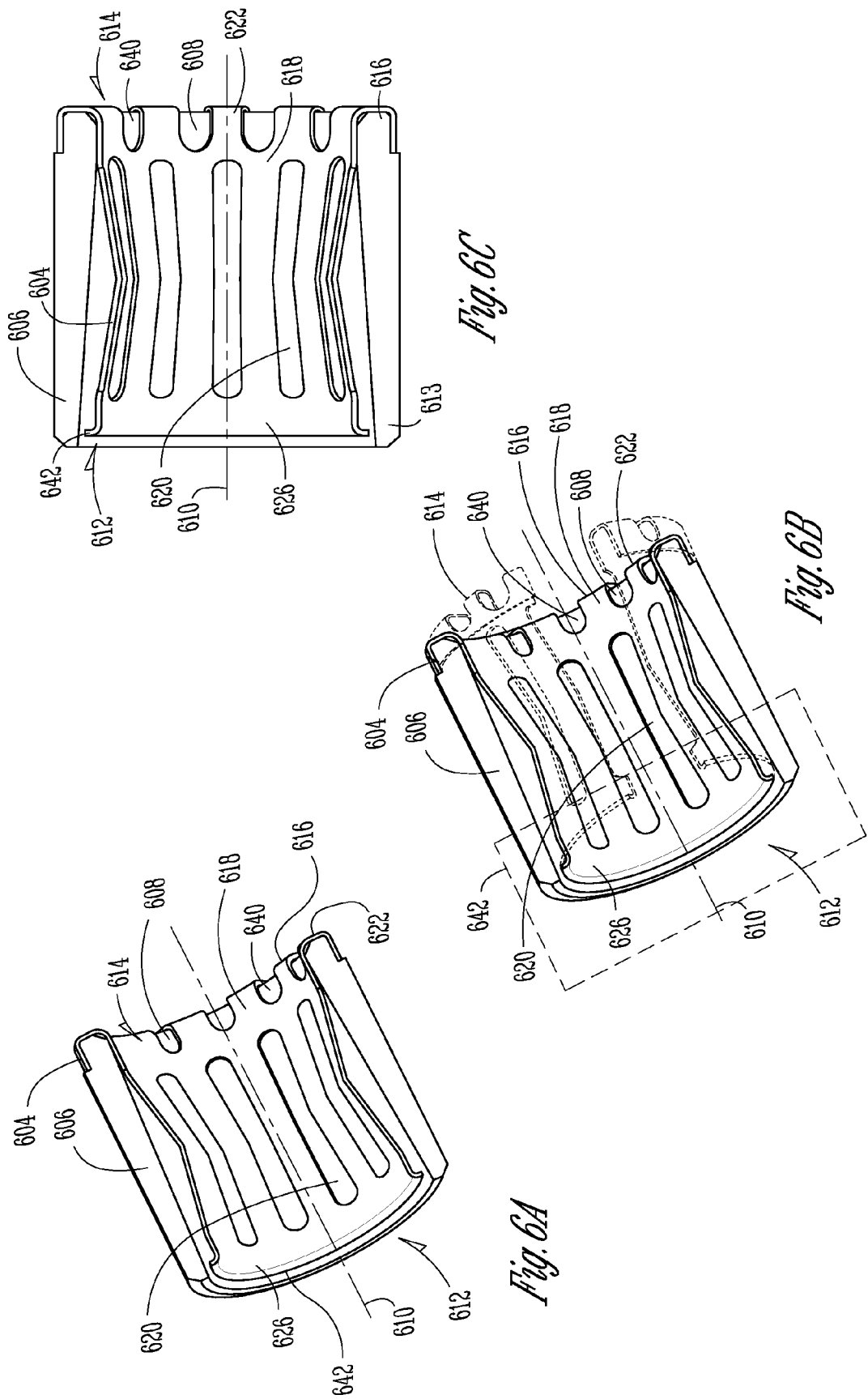
FIG. 6A shows a perspective view of a cross section of a spring that wraps around a housing, according to some examples.
FIG. 6B shows a perspective view of a cross section of a spring that wraps around a housing, showing wireframe of the spring, according to some examples.
FIG. 6C shows a longitudinal cross section of a spring that wraps around a housing, according to some examples.

FIGS. 6A-C show a perspective view of a cross section of a spring that wraps around a housing, according to some examples. Various examples include a housing 606, couplable to a header, such as inside the header. In various examples, the housing 606 is tubular in shape and defines a housing passage 608 extending along a longitudinal axis 610, from a proximal portion 612 to a distal portion 614 including a distal lip 616 that defines a distal opening 618.

The electrical contact spring 604 coupled to the housing 606. In various examples, the electrical contact spring is disposed at least partially inside the housing 606. The electrical contact spring 604 is tubular in shape in some examples. In certain examples, the electrical contact spring 604 defines an electrical contact spring passage 620. In some examples, the electrical contact spring passage 620 is concentric to the housing passage 608.

In various examples, the electrical contact spring 604 includes a distal ring portion 622. In various examples, the distal ring portion 622 is disposed adjacent the distal portion 614 of the housing 606. In various examples, the distal ring portion 622 wraps around the distal lip 616. In various examples, the distal ring portion 622 is physically connected to the distal lip 616 outside the housing passage 608. In some examples, the distal ring portion 622 pinches the distal lip 616. Some examples, the distal ring portion 622 defines a plurality of reliefs 640 disposed annularly around the distal ring portion 622. In some examples, the reliefs aid in bending the spring contact 604 around the distal lip 616. In some examples, the proximal ring portion 626 defines a rounded annular flange, with a rounded portion of the flange facing a plane 642 defined by the proximal lip.

Figure 7:
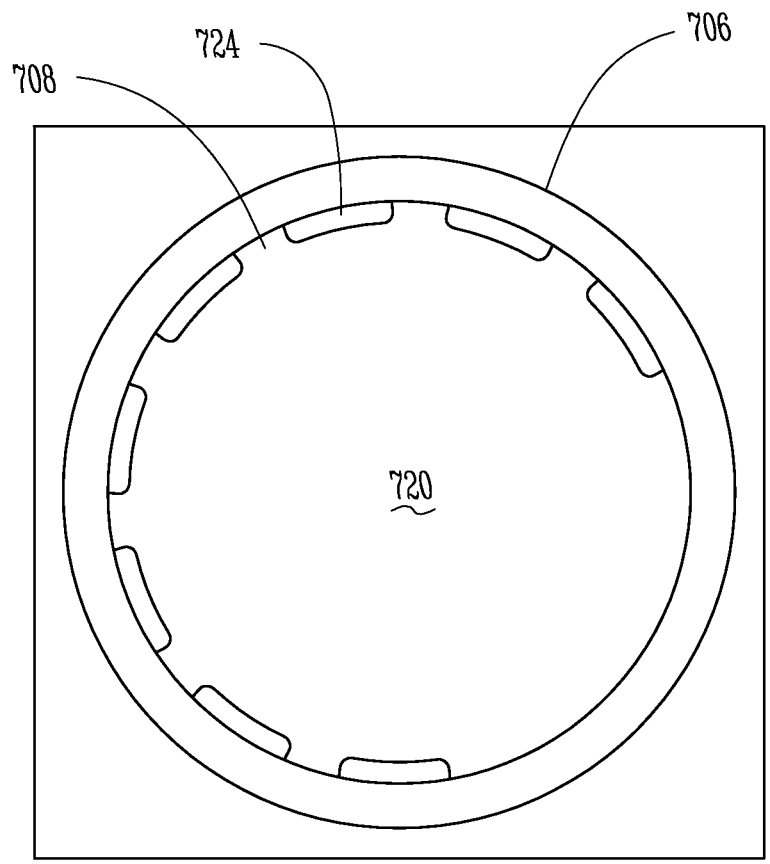
FIG. 7 shows a view along a longitudinal axis of a spring, showing deformation, according to some examples.
Figure 8:
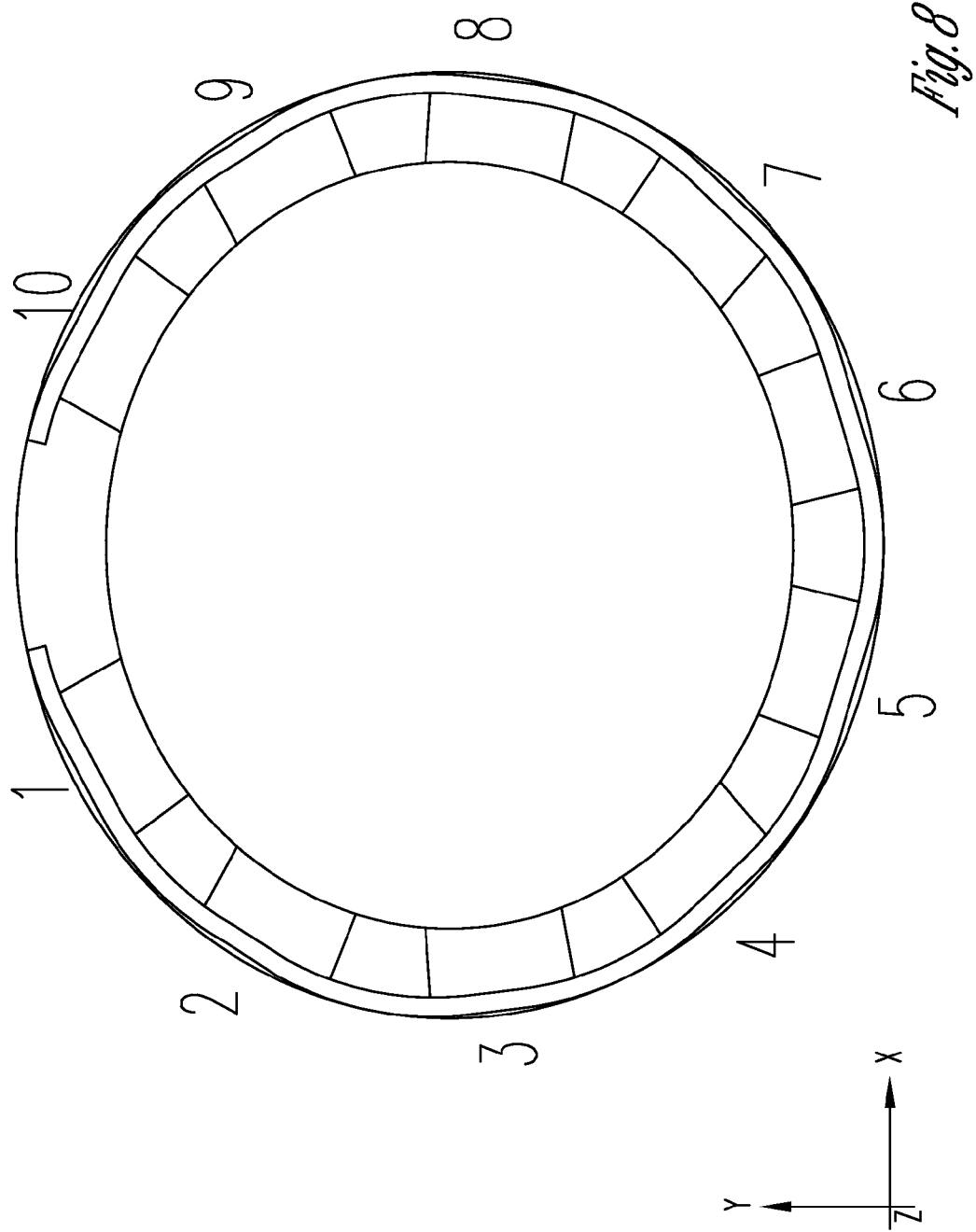
FIG. 8 shows a finite element analysis showing stress on a spring, according to some examples.
Figure 9:
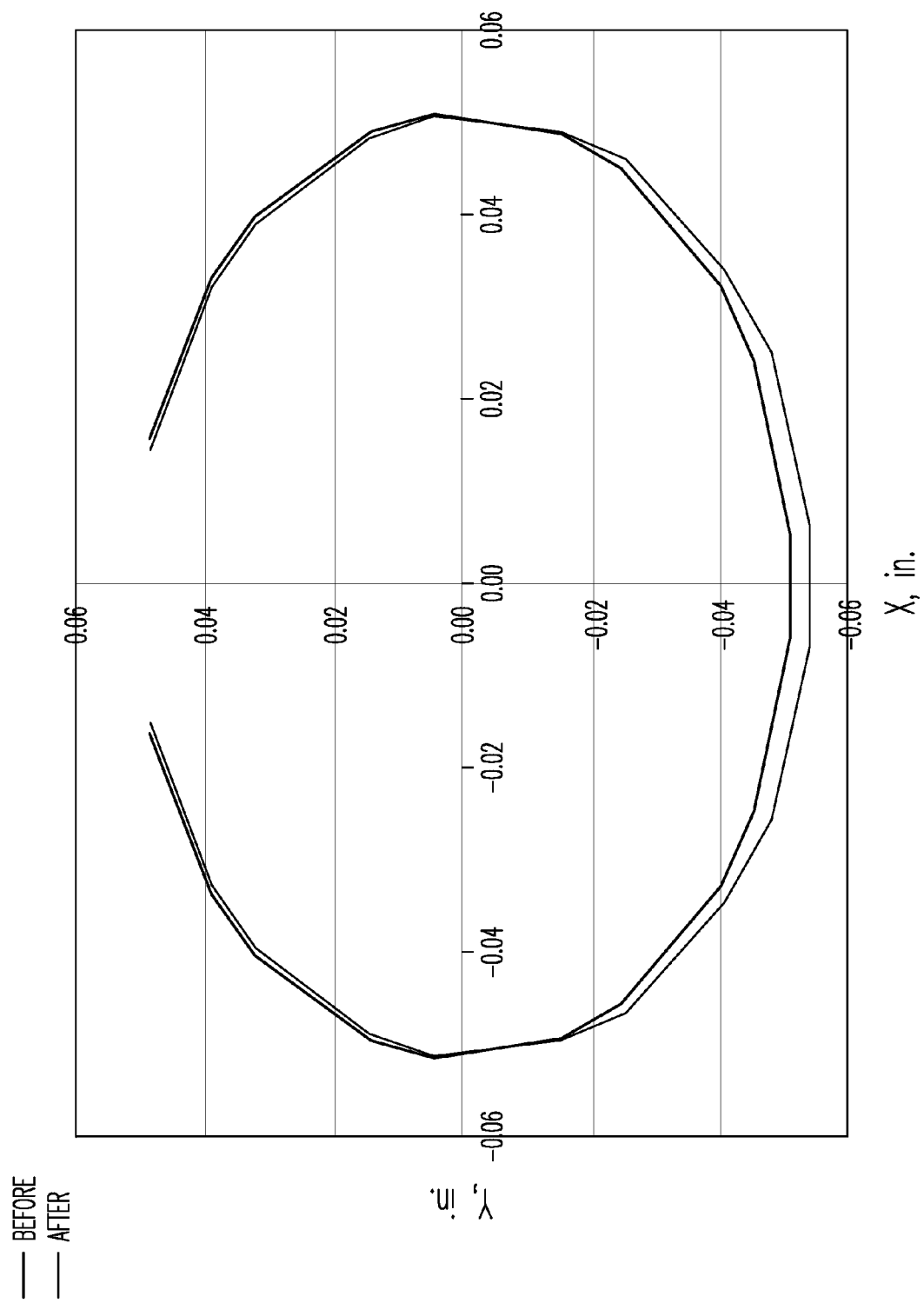
FIG. 9 shows permanent deflection of a first spring design, before insertion and after removal of an electrical lead, according to some examples.

FIG. 7 shows a view along a longitudinal axis of a spring, showing deformation, according to some examples. In the illustration, spring contacts 724 are inelastically deformed with respect to the contact housing 706. In various examples, this places the spring passage 720 out of a selected concentricity with the housing passage 708. In some examples, such inelastic deformation is the result of a distal ring portion and a proximal ring portion each coupled with the spring housing 706. Examples discussed herein, in which only one of the distal ring portion and a proximal ring portion are coupled with the housing, alleviate instances of inelastic deformation. FIG. 8 shows a finite element analysis showing stress on a spring, according to some examples. The figure correlates to examples in which a distal ring portion and a proximal ring portion each are coupled with the spring housing. FIG. 9 shows permanent deflection of a first spring design, before insertion and after removal of an electrical lead, according to some examples. The figure correlates to examples in which only one of the distal ring portion and a proximal ring portion are coupled with the housing.

Figure 10:
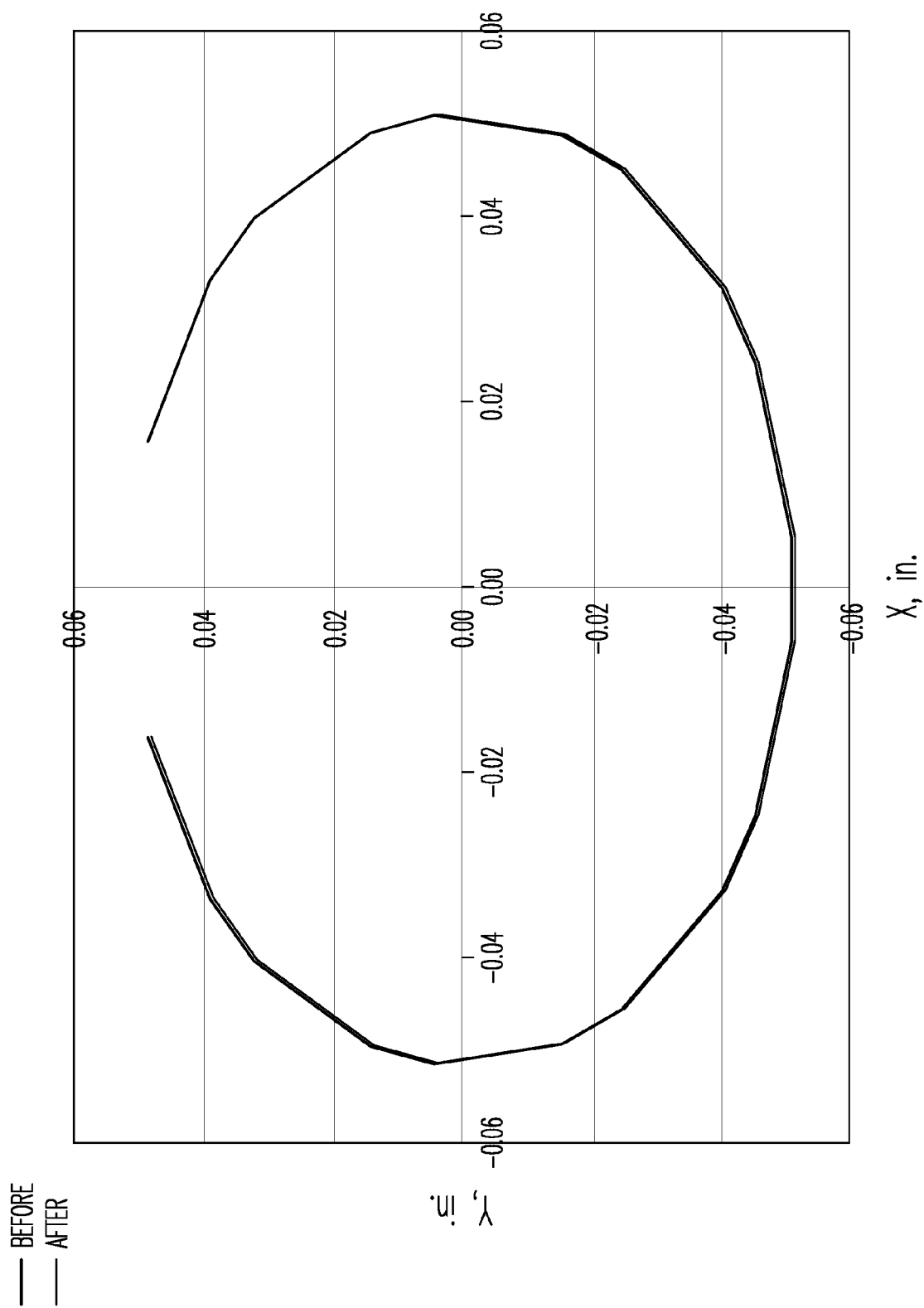
FIG. 10 shows permanent deflection of a first spring design, before insertion and after removal of an electrical lead, according to some examples.
Figure 11:
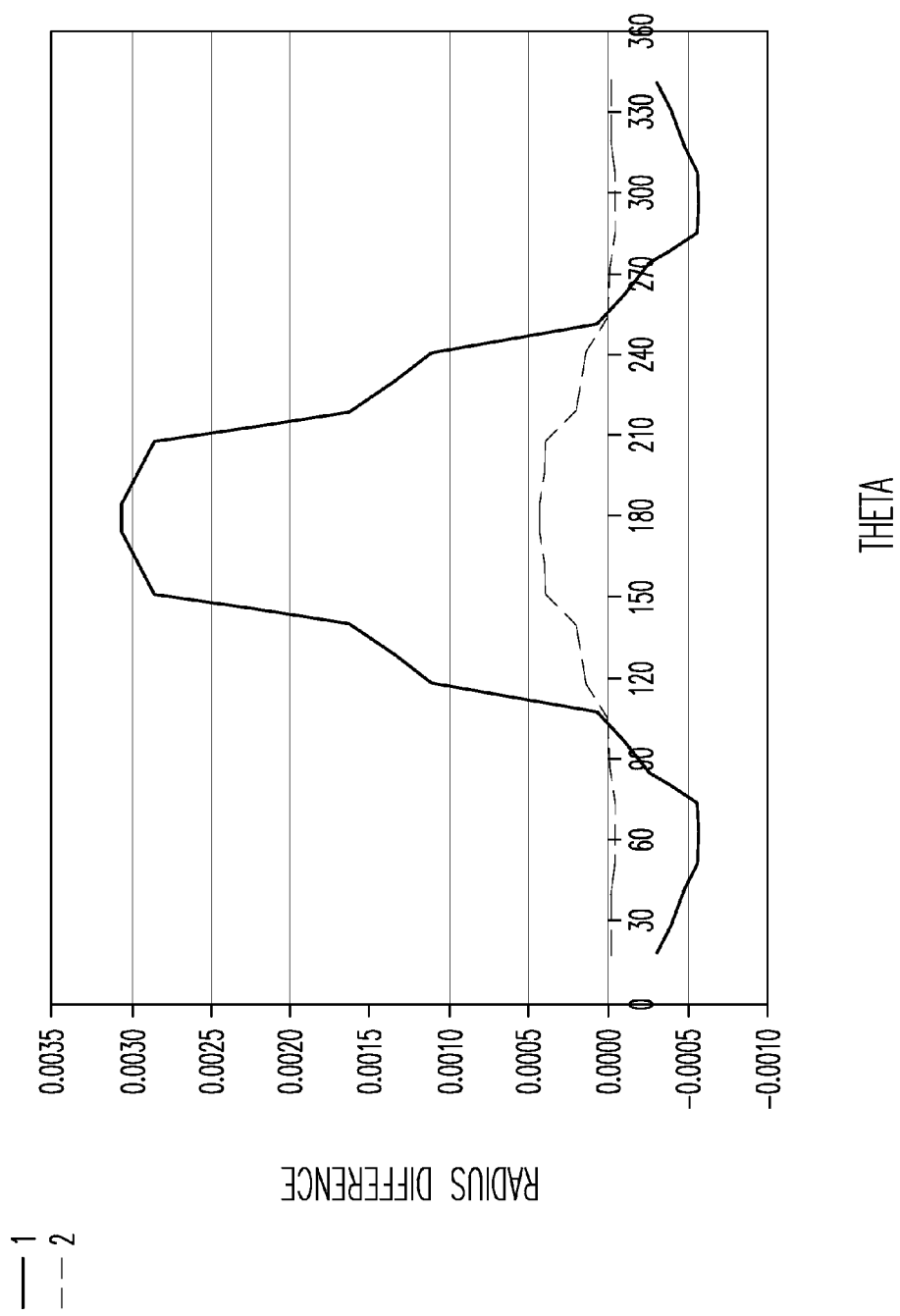
FIG. 11 shows permanent radius differential versus location for a first spring design and a second spring design, according to some examples.

FIG. 10 shows permanent deflection of a first spring design, before insertion and after removal of an electrical lead, according to some examples. The figure correlates to examples in which a distal ring portion and a proximal ring portion each are coupled with the spring housing. FIG. 11 shows permanent radius differential versus location for a first spring design and a second spring design, according to some examples. The figure correlates to examples in which only one of the distal ring portion and a proximal ring portion are coupled with the housing.

Figure 12A:
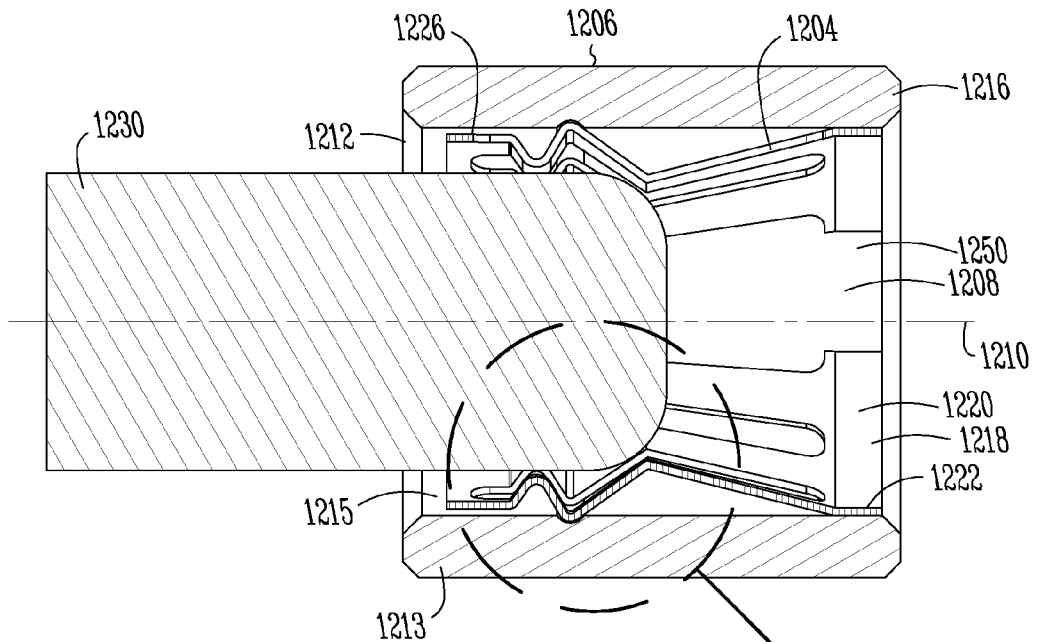
FIG. 12A shows a cross section side view of a non-deflected two-contact spring and a housing, according to some examples.
Figure 12B:
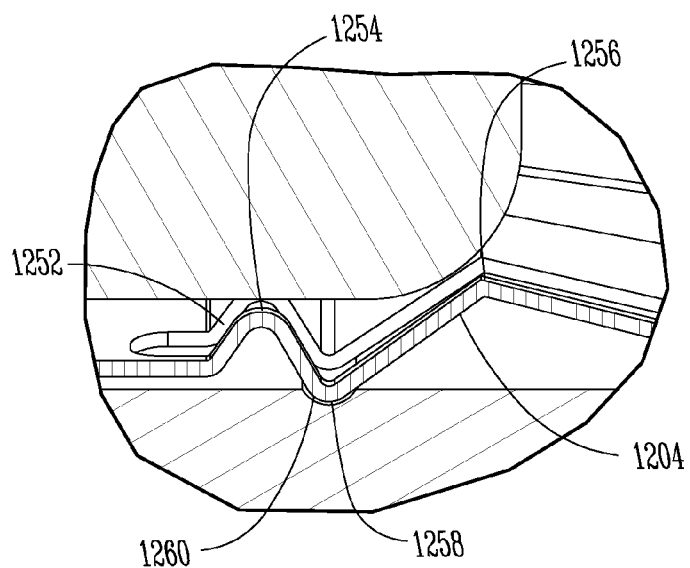
FIG. 12B shows section 12B as depicted in FIG. 12A.
Figure 13A:
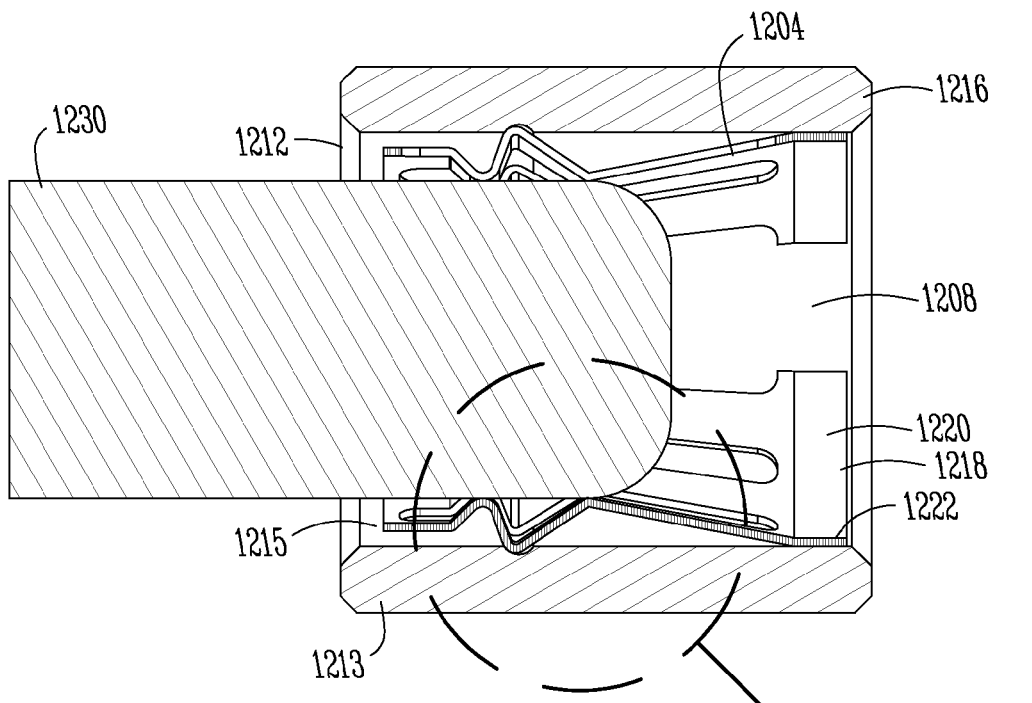
FIG. 13A shows a cross section side view of a deflected two-contact spring and a housing, according to some examples.
Figure 13B:
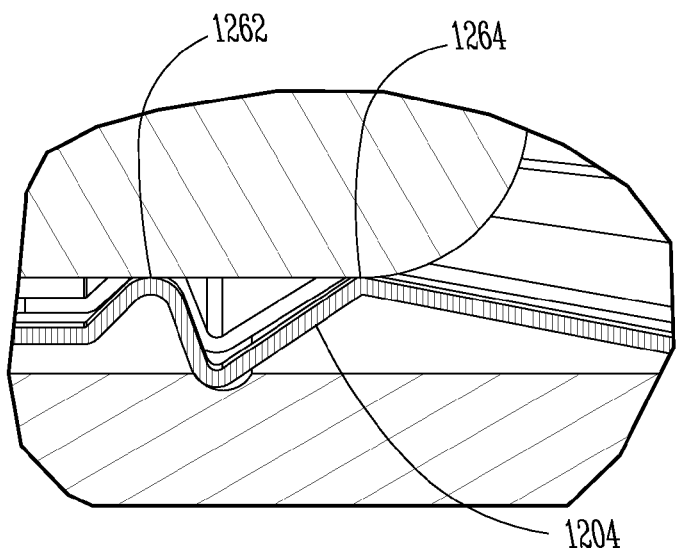
FIG. 13B shows section 12B as depicted in FIG. 13A.

FIGS. 12A-B show a cross section side view of a non-deflected two-contact spring and a housing. FIGS. 13A-B show the two-contact spring deflected. Various examples include a housing 1206, couplable to a header, such as inside the header. In various examples, the housing 1206 is tubular in shape and defines a housing passage 1208 extending along a longitudinal axis 1210, from a proximal portion 1212 including a proximal lip 1213 that defines a proximal opening 1215, to a distal portion 1214 including a distal lip 1216 that defines a distal opening 1218.

The electrical contact spring 1204 coupled to the housing 1206. In various examples, the electrical contact spring is disposed at least partially inside the housing 1206. The electrical contact spring 1204 is tubular in shape in some examples. In certain examples, the electrical contact spring 1204 defines an electrical contact spring passage 1220. In some examples, the electrical contact spring passage 1220 is concentric to the housing passage 1208.

In various examples, the electrical contact spring 1204 includes a distal ring portion 1222. In various examples, the distal ring portion 1222 is disposed adjacent the distal portion 1214 of the housing 1206. In some examples, the distal ring portion 1222 abuts the housing 1206. In some examples, the distal ring portion 1222 is physically coupled to the housing 1206. Examples of such a physical coupling include, but are not limited to, an adhesive, a press fit, a threaded engagement, a weld, including a spot weld, and instances in which the electrical contact spring 1204 is formed integrally with the housing 1206, that is, they are formed from the same starting material.

Various examples include a proximal ring portion 1226 disposed near the proximal portion 1212 of the housing 1206, suspended inside of and spaced apart from at least some of the housing 1206 by an electrical spring contact 1204 that includes a plurality of electrical contact spring elements 1224 coupled to and extending from the distal ring portion 1222 toward the proximal portion of the housing. In various examples, the plurality of electrical contact spring elements 1224 are adapted to flex to move transversely 1228 with respect to the longitudinal axis, to move the proximal ring portion 1226 with respect to the housing 1206. In various examples, the proximal opening 1215 is larger than a perimeter or circumference of the proximal ring portion 1226, according to some examples.

According to some examples, the plurality of electrical contact springs 1204 fully circumscribe the electrical contact spring passage 1220. In some examples, the do not fully circumscribe the electrical contact spring passage 1220, and instead define a c-shape along a cross section transverse to the longitudinal axis 1210, with two ends meeting at a gap 1250.

In various examples, one or more of the plurality of electrical contact springs 1204 includes a levered portion 1252. The levered portion, in some examples, includes an internal proximal apex 1254 and an internal distal apex 1256, with a outer apex 1258 disposed longitudinally between the internal proximal apex 1254 and the internal distal apex 1256. The internal apexes are disposed nearer the longitudinal axis 1210 than is the outer apex. In various examples, the outer apex 1258 is seated in a channel 1260 disposed in the housing 1206.

According to some examples, the outer apex 1258 serves as a fulcrum around which the internal distal apex 1256 and the internal proximal apex 1254 rotate around to communicate mechanical force from one to the other. As such, depression of the internal distal apex 1256 away from the longitudinal axis 1210 brings the internal proximal apex 1254 nearer to the longitudinal axis 1210. In some examples, when the lead and the plurality of electrical contact springs are sized such that insertion of the lead 1230 into the electrical contact passage 1220 to displace one or more internal distal apexes 1256 clamps the lead 1230 with one or more internal proximal apexes 1254 by rotating the electrical contact spring 1224 around the fulcrum of the outer apex 1258. The clamping of the lead provides two contact points 1262, 1264 to contact the electrical lead 1230. In some cases, the electrical contact springs additionally elastically or plastically deform to accommodate the lead 1230.

Figure 14:
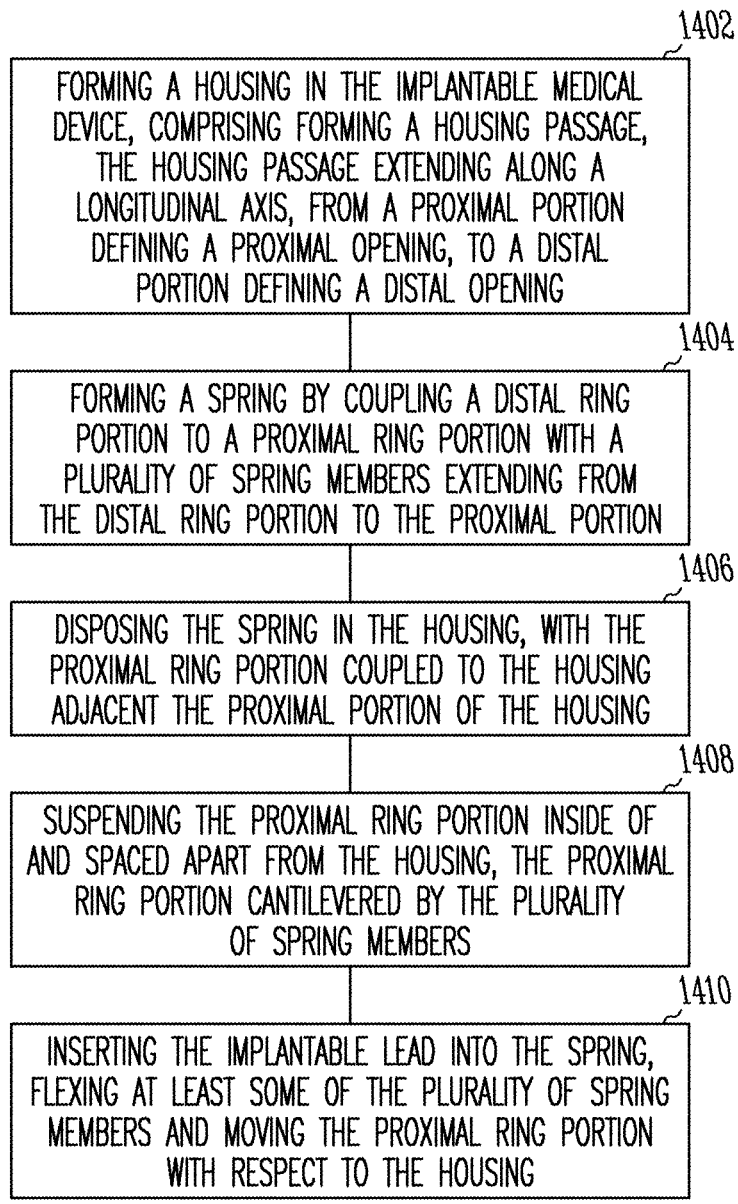
FIG. 14 shows a method for connecting an implantable electrical lead to an implantable medical device, according to some examples.

FIG. 14 shows a method for connecting an implantable electrical lead to an implantable medical device, according to some examples. At 1402, the method includes forming a housing in the implantable medical device, comprising forming a housing passage, the housing passage extending along a longitudinal axis, from a proximal portion defining a proximal opening, to a distal portion defining a distal opening, according to some examples. At 1404, the method includes forming an electrical contact spring by coupling a distal ring portion to a proximal ring portion with a plurality of electrical contact spring elements extending from the distal ring portion to the proximal portion, according to some examples. At 1406, the method includes disposing the electrical contact spring in the housing, with the proximal ring portion coupled to the housing adjacent the proximal portion of the housing, according to some examples. At 1408, the method includes suspending the proximal ring portion inside of and spaced apart from the housing, the proximal ring portion cantilevered by the plurality of electrical contact spring elements, according to some examples. At 1410, the method includes inserting the implantable electrical lead into the electrical contact spring, flexing at least some of the plurality of electrical contact spring elements and moving the proximal ring portion with respect to the housing, according to some examples.

Some methods include flexing the proximal ring portion out of concentric alignment with the housing when an longitudinal axis of the implantable electrical lead is skew to the longitudinal axis. Some methods include sizing the proximal opening of the housing to receive the electrical lead terminal therethrough with a non-contact clearance. Some methods include elastically deforming the plurality of electrical contact spring elements with the proximal ring portion abutting at least a portion the housing. Some methods include forming the spring by stamping sheet metal. Some methods include forming the spring by rolling the sheet metal. Some methods include forming the spring by bending the sheet metal. Some methods include forming the distal ring portion, the proximal ring portion and the plurality of spring elements from a single piece of material, each integral with the another.

The present subject matter is described in connection with its use as a terminal of an implantable medical device for connecting and releasing, such as by hand pressure, the proximal portion of an electrical lead to an implantable heart pacemaker. The present subject matter is not so limited, and has broader applicability to electrical terminals generally, irrespective of the device to which the electrical lead is to be connected.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An apparatus, comprising:
   a housing that is rigid, defining a housing passage extending along a longitudinal axis, from a proximal portion including a proximal lip that defines a proximal opening, to a distal portion including a distal lip that defines a distal opening, the housing including an inner surface; and an electrical contact spring disposed in the housing, the electrical contact spring defining an electrical contact spring passage concentric to the housing passage, the electrical contact spring comprising:
- a distal ring portion disposed adjacent the distal portion of the housing and physically coupled to the housing;
- a proximal ring portion disposed near the proximal portion of the housing, the proximal ring portion being cantilevered and suspended inside of the housing and spaced apart from the inner surface of the housing, and a plurality of electrical contact spring elements coupled to and extending from the distal ring portion to the proximal ring portion.

2. The apparatus of claim 1, wherein each of the plurality of electrical contact spring elements includes a respective center portion extending toward the longitudinal axis of the housing, nearer the longitudinal axis than is the distal ring portion.

3. The apparatus of claim 2, wherein each respective center portion extends toward the longitudinal axis of the housing, nearer the longitudinal axis than the proximal ring portion.

4. The apparatus of claim 1, wherein the distal lip is of a diameter smaller than a diameter of an opening defined by the distal ring portion, and the housing includes a interior portion, adjacent the distal lip, of a diameter larger than the diameter of the opening defined by the distal ring portion, with the electrical contact spring physically coupled to the interior portion.

5. The apparatus of claim 1, wherein the proximal lip is of a diameter that is approximately equal to a diameter of the proximal ring portion.

6. The apparatus of claim 5, wherein the housing includes an interior portion of a diameter greater than the diameter of the proximal lip.

7. The apparatus of claim 1, wherein the proximal lip is of a diameter greater than a diameter of the proximal ring portion of the electrical contact spring.

8. The apparatus of claim 1, wherein the distal ring portion is wrapped around the distal lip.

9. The apparatus of claim 8, wherein the distal ring portion is physically connected to the distal lip outside the housing passage.

10. The apparatus of claim 1, wherein the proximal ring portion defines a rounded annular flange, with a rounded portion of the flange facing a plane defined by the proximal lip.

11. The apparatus of claim 1, wherein each respective center portion is nearer the longitudinal axis of the housing than other portions thereof.

12. The apparatus of claim 1, wherein at least one electrical spring contact includes an internal proximal apex, an internal distal apex, and an outer apex disposed longitudinally between the internal proximal apex and the internal distal apex, wherein the electrical contact spring is configured to rotate the internal proximal apex toward the longitudinal axis when the internal distal apex is rotated away from the longitudinal axis.

13. A system, comprising:
- a hermetically sealed implantable medical device;
- a header coupled to the hermetically sealed medical device;
- a housing, coupled to the header, inside the header, the housing tubular in shape, defining a housing passage extending along a longitudinal axis, from a proximal portion including a proximal lip that defines a proximal opening, to a distal portion including a distal lip that defines a distal opening, the housing including an inner surface; and
- an electrical contact spring disposed in the housing, the electrical contact spring tubular in shape and defining an electrical contact spring passage concentric to the housing passage, the electrical contact spring comprising:
- a distal ring portion disposed adjacent the distal portion of the housing and physically coupled to the housing;
- a proximal ring portion disposed near the proximal portion of the housing, the proximal ring portion suspended inside of and spaced apart from at least some of the inner surface of the housing, and a plurality of electrical contact spring elements coupled to and extending from the distal ring portion to the proximal ring portion, wherein the plurality of electrical contact spring elements are adapted to flex to move transversely with respect to the longitudinal axis, to move the proximal ring portion with respect to the housing; and
- an electrical lead disposed in the electrical contact spring passage, with at least some of the plurality of electrical contact spring elements deformed around the electrical lead, contacting an electrical contact of the electrical lead.

14. The system of claim 13, wherein each respective center portion physically contacts the electrical lead in electrical conduction when the electrical lead is inserted into the electrical contact spring passage, substantially aligned with the longitudinal axis.

15. The system of claim 13, wherein the header is molded around the housing.

16. The system of claim 13, wherein the proximal lip is sized to receive the electrical lead without contacting the electrical lead.

* * * * *